Figure 1:
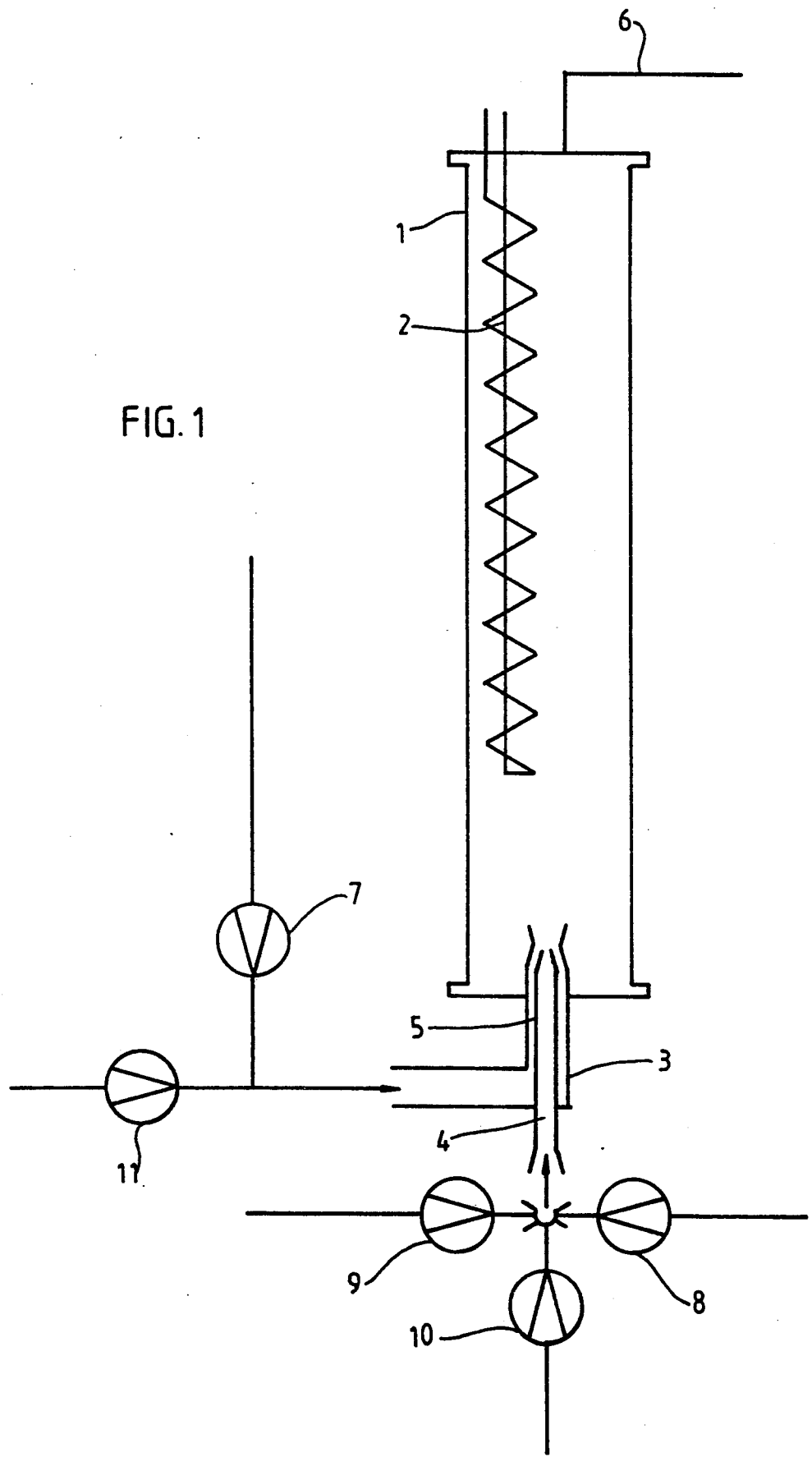

United States Patent [19]

Steffan

[11] Patent Number: 5,144,065

[45] Date of Patent: Sep. 1, 1992

[54] PROCESS FOR THE PREPARATION OF AMINOARYLSULPHONIC ACIDS

[75] Inventor: Guido Steffan, Odenthal, Fed. Rep. of Germany

[73] Assignee: Bayer Aktiengesellschaft, Leverkusen, Fed. Rep. of Germany

[21] Appl. No.: 737,635

[22] Filed: Jul. 30, 1991

[30] Foreign Application Priority Data

Aug. 8, 1990 [DE] Fed. Rep. of Germany ....... 4025131

[51] Int. Cl.$^5$ ................. C07C 303/22; C07C 309/29; C07C 309/35
[52] U.S. Cl. ...................................... 562/68; 562/58; 562/72
[58] Field of Search ............................ 562/58, 68, 72

[56] References Cited

U.S. PATENT DOCUMENTS 4,163,752  8/1979  Barth et al. ............................ 562/68
4,503,276  3/1985  Nickson .................................. 562/58

*Primary Examiner*—Marianne Cintins
*Attorney, Agent, or Firm*—Sprung Horn Kramer & Woods

[57] ABSTRACT

In the process according to the invention for the preparation of aminoarylsulphonic acids by catalytic hydrogenation of nitroarylsulphonic acids, a substantial increase in the space-time yield in combination with reduced consumption of the catalyst is achieved by dispersing the hydrogen more finely and by limiting according to the invention the concentration of the nitroarylsulphonic acids to be hydrogenated.

4 Claims, 1 Drawing Sheet

PROCESS FOR THE PREPARATION OF AMINOARYLSULPHONIC ACIDS invention relates to a new process for the preparation of aminoarylsulphonic acids by catalytic hydrogenation of nitroarylsulphonic acids.

Various processes for the preparation of aminoarylsulphonic acids by catalytic hydrogenation of nitroarylsulphonic acids are already known (see, for example, German Patent Specification 2,703,076, British Patent Specification 1,576,608 and EP-A (European Published Specification) 000,634). Of the processes described in these publications, the processes in which the low-cost nickel catalysts such as Raney nickel and Raney nickel/iron can be used and the use of the expensive noble metal catalysts palladium and platinum is not required are particularly preferred in practice.

However, it was found that the catalytic hydrogenation described in German Patent Specification 2,703,076 and British Patent Specification 1,576,608 of nitroarylsulphonic acids with Raney nickel is not economically feasible on an industrial scale, because the consumption of catalyst is too high and high yields of aminoarylsulphonic acid can only be achieved at the cost of the space-time yield or that the aminoarylsulphonic acids at the required space-time yields necessary for an economic process are obtained only in unsatisfactory yields. Furthermore, it was found that the processes described earlier do not give reproducible results under industrial conditions.

It has now been found that the catalytic hydrogenation of nitroarylsulphonic acids in aqueous media with Raney nickel or Raney nickel/iron is achieved in high yields in combination with a low, economically acceptable consumption of catalyst and in the required high space-time yields if in the known processes the dispersion of the hydrogen required for the reduction in the aqueous catalyst suspensions is substantially increased and at the same time the concentrations selected of the nitroarylsulphonic acid solutions or suspensions to be hydrogenated, which are metered into the aqueous catalyst suspensions, are lower than was previously the case. It was found that the combination of both measures—to disperse the hydrogen more finely and to reduce the concentrations of the nitroarylsulphonic acids to be hydrogenated in the aqueous catalyst suspension—gives a considerably smoother hydrogenation of the nitroarylsulphonic acids to the aminoarylsulphonic acids (=higher (space-time) yields of aminoarylsulphonic acids) in combination with improved retention of catalyst activity (lower consumption of the catalyst).

Accordingly, the invention relates to a process for the preparation of aminoarylsulphonic acids by catalytic hydrogenation of nitroarylsulphonic acids with hydrogen in the presence of Raney nickel or Raney nickel/iron in aqueous media under a hydrogen pressure of 100 to 300 bar and at a temperature of 130° to 160° C., which process is characterised in that the hydrogen is finely dispersed in the aqueous catalyst suspensions such that the primary surface area of the gas bubbles is more than 60,000 $m^2/m^3$ of $H_2$ and in that the nitroarylsulphonic acids are fed into the hydrogenation mixture in the form of aqueous solutions or suspensions which, depending on the nitroarylsulphonic acid used, contain 0.45 to 0.55 mol of nitroarylsulphonic acid per kg of solution or suspension.

The hydrogen is finely dispersed according to the invention in the aqueous catalyst suspensions at a surface area of >60,000 $m^2/m^3$ of $H_2$, preferably at surface areas (=gas/liquid interfaces) of 600,000 to 6 million $m^2/m^3$ of $H_2$, which corresponds to a primary gas bubble diameter of no more than 100 μm, preferably 10 to 1 μm, in various ways known per se; for example, by injecting hydrogen under pressure into the catalyst suspensions stirred by a high-speed special stirrer, for example a tubular stirrer (number of revolutions in a 7 l laboratory autoclave >2,000 rpm), or by injecting the hydrogen into the pressure vessel by means of a jet nozzle (two-component nozzle).

Dispersion of the hydrogen in the aqueous catalyst suspensions by injection by means of a jet nozzle has proved to be particularly advantageous, because it allows the use of movable parts (stirrer) in the pressure vessel to be omitted and because in addition the aqueous solutions or suspensions of the nitroarylsulphonic acids to be hydrogenated or, in the case of continuous hydrogenation, aqueous catalyst suspensions mixed with the aqueous solutions or suspensions of the nitroarylsulphonic acids can be used as propellants for the jet nozzles, and the injection and dispersion of the hydrogen in the aqueous catalyst suspensions can in this manner be combined with the metering-in of the nitro compounds to be hydrogenated or the continuous metering-in of catalyst suspensions and nitroarylsulphonic acids.

Examples of representatives of the nitroarylsulphonic acids to be hydrogenated according to the invention are:

1-nitronaphthalene-3,6,8-trisulphonic acid (nitro T acid; in pure form or in the form of the nitronaphthalenetrisulphonic acid mixture formed in the naphthalene trisulphonation and subsequent nitration),
3-nitronaphthalene-1,5-disulphonic acid (nitro Armstrong's acid),
1-nitronaphthalene-8-sulphonic acid (nitro peri acid),
1-nitronaphthalene-5-sulphonic acid (Laurent's α-acid),
3-nitrobenzenesulphonic acid.

Of the nitroarylsulphonic acids listed, the following aminosulphonic acids are obtained in the process according to the invention:

1-aminonaphthalene-3,6,8-trisulphonic acid (T acid),
3-aminonaphthalene-1,5-disulphonic acid (C acid),
1-aminonaphthalene-8-sulphonic acid (peri acid),
1-aminonaphthalene-5-sulphonic acid (Laurent's acid) and
3-aminobenzenesulphonic acid.

An essential parameter of the process according to the invention are the concentrations of the solutions of the nitroarylsulphonic acids used for the hydrogenation. It was found that the solutions or suspensions of these nitroarylsulphonic acids must not exceed certain limiting concentrations which are different for the individual nitroarylsulphonic acids. In the table below, these limiting concentrations and the concentration ranges preferably used in the process according to the invention are listed for the individual nitroarylsulphonic acids. These limiting concentrations are determined by preliminary tests.

TABLE

| Nitroarylsulphonic acid | Limiting concentration [mol/kg*] | Limiting concentration [% by wt.] | Preferred concentration range [mol/kg] | Preferred concentration range [% by wt.] |
| --- | --- | --- | --- | --- |
| Nitro T acid | | | 0.4–0.46 | 16.5–19 |
| Nitronaphthalene-tri-sulfphonic acid mixture MW 413 | 0.48 | 19.8 | | |
| Nitro Armstrong's acid | 0.55 | 18.3 | 0.45–0.5 | 15–17 |
| Nitro peri/Laurent's acid | 0.52 | 13.2 | 0.45–0.5 | 11–13 |
| 3-Nitrobenzenesulphonic acid | 0.45 | 9.2 | 0.40–0.44 | 8–9 |

*Solution or suspension

The process according to the invention can be carried either batchwise or continuously.

The batchwise procedure can be carried out, for example, as follows:

Raney nickel catalyst and water are initially introduced into a pressure vessel (autoclave) equipped with a high-speed stirrer (for example a tubular stirrer) and heating and cooling elements. After displacing the air from the autoclave by successive flushing of the apparatus with nitrogen and hydrogen, hydrogen is injected into the autoclave up to a pressure of 50 bar. The contents of the pressure vessel are rapidly heated to 150° C. with stirring at normal rotational speed (about 500 rpm). The hydrogen pressure in the autoclave is then adjusted to 150 bar, the stirring speed is increased to 2,500 rpm, and the solution (suspension) of the nitroarylsulphonic acid to be hydrogenated is metered in at a rate which corresponds approximately to the rate of hydrogenation (=rate at which the nitroarylsulphonic acid is hydrogenated to the aminoarylsulphonic acid). During the metering-in of the nitroarylsulphonic acid, the pressure in the autoclave increases to about 200 bar, and the temperature of the autoclave contents is kept at 150° C. by temporary cooling. After addition of the nitroarylsulphonic acid is completed, the hydrogenation mixture is stirred for an additional short period, about 5 to 10 minutes, under the pressure and at the temperature given at a high rotational speed. The rotational speed is then reduced again to a normal rotational speed (about 500 rpm), and the autoclave contents are cooled to 50° C. The stirrer is then turned off to allow the catalyst to settle. After the pressure vessel has been let down, the catalyst-free aqueous solution of the aminoarylsulphonic acid is removed from the pressure vessel except for an amount required for suspending the settled catalyst for the next batch and worked up in the usual manner. The suspension of the used catalyst remaining in the pressure vessel in the aqueous solution of the aminoarylsulphonic acid is used as an initial mixture for the next hydrogenation batch, if appropriate after adding 1 to 2% by weight of fresh catalyst, relative to the weight of the used catalyst.

It is possible to connect two or more of the batchwise-operated reactors described above in series to give a reactor cascade.

Continuous operation of the process according to the invention can be carried out, for example, in the pressure reactor (1) which is shown schematically in FIG. 1 and equipped with a heating/cooling device (2) and a jet nozzle (3). The liquid reaction components, the catalyst suspension (the circulated catalyst suspension and fresh catalyst suspended in water) and the solution or suspension of the nitroarylsulphonic acids to be hydrogenated are introduced into the reactor (1) via the inner tube (4) of the jet nozzle, while the hydrogen (fresh hydrogen and recirculated hydrogen) is introduced via the outer tube (5) of the jet nozzle, which concentrically surrounds the inner tube (4). The suspension of the catalyst saturated with finely dispersed hydrogen and present in the aqueous solution of the aminoarylsulphonic acids is continuously removed from the reactor (1) via line (6).

After this suspension discharged continuously from the reactor (1) has been separated into hydrogen, aqueous solution of the aminoarylsulphonic acid and concentrated suspension of the catalyst in aqueous aminoarylsulphonic acid solution, the recovered hydrogen (recirculated hydrogen), the concentrated suspension of the used catalyst in the aqueous aminoarylsulphonic acid solution, after a certain amount of used catalyst has been discharged, together with the suspension of fresh catalyst metered in via high-pressure pump (9) and the aqueous suspension or solution of the nitroarylsulphonic to be hydrogenated metered in via high-pressure pump (10) are recirculated or metered (fresh products) into the hydrogenation reactor (1) via jet nozzle (3) by means of a circulating compressor (7) in the case of hydrogen and by means of a high-pressure pump (8) in the case of the metered-in product.

In the procedure described, the hydrogen is finely dispersed in the aqueous catalyst suspension only after the latter has been mixed with the aqueous solution or suspension of the nitroarylsulphonic acid. However, since the period after which the hydrogen is finely dispersed in the catalyst suspension mixed with the nitroarylsulphonic acid is extremely short and the mixing of the aqueous catalyst suspension with the aqueous solution or suspension of the nitroarylsulphonic acid is carried out at temperatures of 30° to 60° C., i.e. far below the hydrogenation temperature, this type of procedure also does not lead to a loss of catalyst activity.

The hydrogenation reactor is operated under a hydrogen pressure of 100 to 200 bar. The compressors and high-pressure pumps (7) to (11) and the dimensions of the jet nozzle are set to such a value that the hydrogen is finely dispersed according to the invention in the suspension of the catalyst in the aqueous solution of the hydrogenation mixture at >60,000 m$^2$ of primary 9as surface area/m$^3$ of H$_2$. The process is preferably carried out such that the hydrogen is finely dispersed in the catalyst suspensions at 600,000 to 6 million m$^2$ of primary gas surface area/m$^3$ of H$_2$.

It is also possible to connect more than one, for example three, of the hydrogenation reactors (1) described above in series to give a reactor cascade.

The Raney nickel catalysts used in the process according to the invention are the known Raney nickel and Raney nickel/iron catalysts.

In continuous hydrogenations of nitroarylsulphonic acids to aminoarylsulphonic acids, the catalysts are used in conventional amounts of 1 to 5% by weight, relative to the weight of the nitroarylsulphonic acid solutions to be hydrogenated. 1 to 4, preferably 1.5 to 2.5, % by weight of this catalyst amount should be fresh catalyst, while the remainder, 98.5 to 97.5% by weight, should be used catalyst.

In batchwise hydrogenations, catalyst concentrations of about 0.2–1% by weight, relative to the weight of the nitroarylsulphonic acid solutions to be hydrogenated, are preferably used, which allows the hydrogenation of a large number of batches (see examples) with one charge of the catalyst. (The number of batches of a campaign can be increased here too by additional metering-in of small amounts of fresh catalyst).

The aqueous solutions or suspensions of the nitroarylsulphonic acids to be hydrogenated should have a pH in the range from 7 to 9.5.

The hydrogenation according to the invention is carried out at temperatures of 100° to 180° C., preferably 130° to 160° C., and pressure of 100° to 300 bar, preferably 130° to 200° bar.

EXAMPLE 1

The hydrogenation was carried out in the hydrogenation reactor shown schematically in FIG. 1 (inner diameter of the reactor: 400 mm; height: 6,900 mm; as a result of the built-in heating and cooling devices, effective volume of the reactor was only about 730 l).

The hydrogen is first finely dispersed in the aqueous catalyst suspension at 600,000 to 6 million $m^2/m^3$ of $H_2$ by means of a jet nozzle. 3.5 $m^3$ (about 4.03 tonnes) of a solution containing 0.42 mol = 17.4% by weight of a 1-nitronaphthalene-trisulphonic acid mixture of the following composition 82% by weight of 1-nitronaphthalene-3,6,8-trisulphonic acid,
11% by weight of 1-nitronaphthalene-3,5,7-trisulphonic acid,
4.5% by weight of 1-nitronaphthalene-4,6,8-trisulphonic acid,
1.7% by weight of 1-nitronaphthalene-2,5,7-trisulphonic acid and
about 1% by weight of 2-nitronaphthalene-3,5,7-trisulphonic acid per kg of solution were pumped into the reactor (1) per hour by means of the high-pressure pump (10). (pH of the solution: 7.5 to 8). 1.7 $m^3$ of the suspension of the used catalyst discharged via line (6) and concentrated to a Raney nickel content of about 6% by weight in the aqueous aminonaphthalenesulphonic acid solution and about 2.8 kg of fresh Raney nickel suspended in water were pumped in per hour via the high-pressure pump (8) and high-pressure pump (9), respectively, at the same time as the nitronaphthalenetrisulphonic acid solution.

The temperature in the reactor was 150° C. and the pressure 200 bar. About 3,000 $Nm^3$ of hydrogen were circulated and about 120 $Nm^3$ of fresh hydrogen were fed in per hour. The conversion of nitro compounds was more than 99.5%, and the yield of aminonaphthalenetrisulphonic acids 98% of theory. The catalyst consumption was 0.4% by weight, relative to the weight of the nitronaphthalenetrisulphonic acids.

If the concentration of the nitronaphthalenetrisulphonic arids was increased from 0.42 mol/kg of solution = 17.4% by, weight to 19.2% by weight, the catalyst consumption already increased to 1.5 times, i.e. to 0.6% by weight. A further increase in the concentration of the nitronaphthalenesulphonic acid solution increased the catalyst consumption over proportionately, and the concentration and separation of the catalyst from the hydrogenation solution became increasingly more difficult, due to agglutination of the catalyst.

EXAMPLE 2

The hydrogenation apparatus used was a 7 l V4A autoclave which was equipped with a tubular stirrer for introduction of gas (rotational speed up to 2,500 rpm), an interior coil for steam heating or water cooling, a shortened riser (for partial discharge) and a long riser (reaching to the bottom of the autoclave) for complete discharge.

1,000 ml of water and 20 g of Raney nickel (100% pure) were initially introduced into this reactor. After flushing the autoclave with nitrogen and hydrogen, the hydrogen pressure was increased to 50 bar, and the autoclave contents were rapidly heated to 150° C. at a stirrer speed of 500 rpm. The pressure was then adjusted to 150 bar with hydrogen, the stirrer speed was increased to 2,500 rpm (hydrogen finely dispersed in the catalyst suspension at about 100,000 to 4 million $m^2$ of primary gas surface area/$m^3$ of $H_2$) and a suspension of nitro Armstrong's acid (magnesium salt) containing 0.48 mol/kg suspension (=16% by weight) (pH of the suspension: 9.5) was pumped into the autoclave over a period of 15 minutes. The pressure reached about 200 bar; the temperature was maintained at 150° C. by occasional cooling.

After the addition of the nitro Armstrong's acid—magnesium salt suspension—had been completed, the mixture was stirred at the temperature mentioned and the pressure mentioned for another 10 minutes at the high rotational speed mentioned, and the rotational speed was then reduced to 500 rpm.

The contents of the autoclave were cooled to 50° C. and then allowed to stand for 1 hour without stirring in order to allow the catalyst to settle. The pressure in the autoclave was then let down to 10 bar, and the catalyst-free aqueous aminonaphthalinedisulphonic acid solution forced out of the autoclave via the short riser and worked up in the usual manner.

The amount remaining in the autoclave of 800 ml of aqeous aminonaphthalenedisulphonic acid solution and catalyst was used as initial mixture for the next batch. In this manner, a total of 16 batches of nitronaphthalenedisulphonic acid were hydrogenated in the manner described using the 20 g of Raney nickel. The yield of C acid was 98.3% of theory, relative to nitro C acid used.

The catalyst consumption was 0.26% by weight, relative to the nitro compound used.

The content of non-reduced nitro compound in the individual batches was about 0.5 g/l in the first batch and rose to about 2.5 g/l by the sixteenth batch.

The pH of the aqueous solutions in the batches after the hydrogenation was 8.5.

The use of a more highly concentrated suspension of the magnesium salt of nitro Armstrong's acid gave a significantly lower yield (only about 82% of theory) and the catalyst activity very rapidly declined.

EXAMPLE 3

The procedure described in Example 2 was repeated, using the pressure apparatus described in Example 2, except that 1000 ml of water and 14 g of Raney nickel/iron (85/15) (100% pure) were initially introduced into the autoclave and an aqueous solution of a mixture of nitro peri acid and nitro Laurent's α-acid containing 0.46 mol of nitro peri/Laurent's acid (=12% by weight) per kg were pumped into the autoclave.

12 batches=5,174 g (=20.45 mol) of nitro peri/Laurent's acid could be hydrogenated with the 14 g of Raney nickel/iron. The yield of peri/Laurent's acid was 4,514 g (=20.24 mol), which corresponds to a yield of 99% of theory, relative to nitro peri/Laurent's acid used.

The catalyst consumption was 0.27% by weight, relative to the nitro compound used.

EXAMPLE 4

The procedure described in Example 2 was repeated, using the pressure apparatus described in Example 2.

For the hydrogenation, 15 g of Raney nickel/iron (85/15) were used, and a 0.4 mol/kg (8% strength by weight) aqueous solution of 3-nitrobenzenesulphonic acid (in the form of its sodium salt) was pumped into the autoclave under the conditions described in Example 2.

23 batches=7,475 g (=36.8 mol) of 3-nitrobenzenesulphonic acid could be hydrogenated with the 15 g of Rane nickel/iron.

The yield of metanilic acid was 6,315 g=36.5 mol, which corresponds to 99.2% of theory, relative to nitrobenzenesulphonic acid used.

The catalyst consumption was 0.2% by weight, relative to 3-nitrobenzenesulphonic acid used.

The content of unconverted nitrobenzenesulphonic acid in the metanilic acid obtained in the individual batches was on average 0.02% by weight and rose to 0.6 and 0.8% by weight in the 22nd and 23rd batch, respectively.

Owing to small amounts of sulphide impurities in the 3-nitrobenzenesulphonic acid, it was pretreated with hydrogen peroxide in the following manner before its hydrogenation:

A solution of 2,000 g of sodium 3-nitrobenzenesulphonate in 8,000 g of deionised water was adjusted at 90° C. to a pH of 10 with about 20 g of 50% strength sodium hydroxide solution, and 65 g of hydrogen peroxide solution (17.5% strength) were then added dropwise over a period of about 30 minutes, the mixture was stirred for 15 minutes and finally adjusted to a pH of 8.0 with 15 g of 50% strength sulphuric acid.

I claim:

1. Process for the preparation of aminoarylsulphonic acids by catalytic hydrogenation of nitroarylsulphonic acids with hydrogen in the presence of Raney nickel or Raney nickel/iron in aqueous media under a hydrogen pressure of 100 to 300 bar and at temperatures of 130° to 160° C., comprising finely dispersing the hydrogen in the aqueous catalyst suspensions such that the primary surface area of the gas bubbles is more than 60,000 $m^2/m^3$ of $H_2$ and in that the nitroarylsulphonic acids are fed into the hydrogenation mixture in the form of solutions or suspensions which, depending on the nitroarylsulphonic acid used, contain 0.40 to 0.55 mol of nitroarylsulphonic acid per kg of feed solution or suspension.

2. Process according to claim 1, wherein the hydrogen is dispersed in the aqueous catalyst suspensions such that the obtained surface area (gas/liquid interface) is 600,000 to 6 million $m^2/m^3$ of $H_2$.

3. Process according to claim 1, wherein the content of the individual nitroarylsulphonic acids in the solution or suspension is
   <0.48 mol of nitro T acid,
   <0.55 mol of nitro Armstrong's acid,
   >0.52 mol of nitro peri/Laurent's acid or
   <0.45 mol of 3-nitrobenzene-sulphonic acid per kg of solution (suspension).

4. Process according to claim 1, wherein the content of the individual nitroarylsulphonic acids in the solutions or suspensions is
   <0.4–0.46 mol of nitro T acid,
   <0.45–0.5 mol of nitro Armstrong's acid,
   <0.45–0.5 mol of nitro peri/Laurent's acid or
   <0.40–0.44 mol of 3-nitrobenzenesulphonic acid per kg of solution (suspension).

* * * * *